United States Patent
Shelly et al.

(10) Patent No.: US 12,406,595 B2
(45) Date of Patent: Sep. 2, 2025

(54) SYSTEM AND METHOD FOR ACCLIMATION TO THERAPY

(71) Applicant: KONINKLIJKE PHILIPS N.V., Eindhoven (NL)

(72) Inventors: Benjamin Irwin Shelly, Pittsburgh, PA (US); Daan Anton Van Den Ende, Breda (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 18/083,671

(22) Filed: Dec. 19, 2022

(65) Prior Publication Data

US 2023/0215290 A1    Jul. 6, 2023

Related U.S. Application Data

(60) Provisional application No. 63/294,987, filed on Dec. 30, 2021.

(51) Int. Cl.
*G09B 19/00* (2006.01)
*G16H 20/30* (2018.01)

(52) U.S. Cl.
CPC ........... *G09B 19/003* (2013.01); *G16H 20/30* (2018.01)

(58) Field of Classification Search
CPC .............................. G09B 19/003; G16H 20/30
See application file for complete search history.

(56) References Cited

U.S. PATENT DOCUMENTS

| | | | |
|---|---|---|---|
| 5,645,575 A | 7/1997 | Stangl et al. | |
| 6,012,926 A * | 1/2000 | Hodges | A61M 21/00 434/48 |
| 2006/0246411 A1* | 11/2006 | Yang | G09B 7/00 434/323 |
| 2011/0245633 A1* | 10/2011 | Goldberg | A61B 5/165 600/323 |
| 2011/0258570 A1* | 10/2011 | Bucolo | G09B 5/00 715/771 |
| 2013/0225950 A1* | 8/2013 | Van Elswijk | G16H 10/20 600/309 |
| 2015/0154380 A1* | 6/2015 | Duckworth | G16H 20/30 705/2 |
| 2015/0374940 A1 | 12/2015 | Froehlich et al. | |
| 2017/0116871 A1* | 4/2017 | Castelli | G09B 7/00 |
| 2018/0310867 A1 | 11/2018 | Sivan et al. | |
| 2020/0121873 A1 | 4/2020 | Hudson et al. | |
| 2022/0022973 A1* | 1/2022 | Sundarapandian | A61B 5/02055 |

* cited by examiner

*Primary Examiner* — Peter R Egloff
(74) *Attorney, Agent, or Firm* — Michael W. Haas

(57) ABSTRACT

A method of acclimating a patient to a therapy and a system for carrying out such method. The method includes providing the patient with an initial step of a therapy set up program for the patient to perform and determining at least one step metric. The at least one step metric determined is: a stress level of the patient while performing the initial step, successful completion of the initial step, the time needed to complete the initial step, and/or the quantity of errors made while carrying out the initial step. The method further includes determining a subsequent step for the patient to perform immediately after the initial step based on the at least one step metric and providing the patient with the subsequent step.

6 Claims, 3 Drawing Sheets

SYSTEM AND METHOD FOR ACCLIMATION TO THERAPY

CROSS REFERENCE TO RELATED APPLICATION

This application claims the benefit of U.S. Provisional Patent Application Ser. No. 63/294,987, filed Dec. 30, 2021. This application is incorporated by reference herein.

BACKGROUND OF THE INVENTION

1. Field of the Invention

The disclosed concept pertains to systems for use in acclimating a patient to a therapy. The disclosed concept further pertains to methods for acclimating a patient to a therapy.

2. Description of the Related Art

In many situations in healthcare, a therapy that is delivered to treat a disorder is intrusive and challenging for the patient who is therefore often reluctant to start the treatment. In current times, the traditional visit to a clinic has often been replaced by a "remote set-up" procedure, where patients remotely, and often independently, set up their equipment and initiate the therapy procedure themselves. For example, Positive Airway Pressure (PAP) therapy for obstructive sleep apnea involves sleeping with a mask that delivers air pressure to avoid airway collapse that occurs during obstructive sleep apnea syndrome. For many people, sleeping with a mask is a source of anxiety, which prevents them from setting-up the device and starting the therapy. For certain patients, the setup can also be technically challenging. The combination of both technical challenge and anxiety (or averseness) for the treatment can easily lead to unsuccessful initiation of the therapy. Other examples that can be challenging to set-up or commence include home equipment for physiotherapy, inhalers or nebulizers for asthma therapy or infusion pumps.

The current trend of increasing telehealth and remote interaction leads to clinicians not having hands on patients, so patients that especially struggle with therapy anxiety are often left to fend for themselves when setting up the equipment for a therapy session. Simple procedural setup guides are insufficiently capable of delivering tailored guidance for patients that are struggling with either comprehension or anxiety (or a combination of both) to ensure success of the remote set-up.

Accordingly, there exists a need for improved systems and methods for use in training/acclimating patients to therapies.

SUMMARY OF THE INVENTION

As one aspect of the present invention, a method of acclimating a patient to a therapy is provided. The method comprises: providing the patient with an initial step of a therapy set up program for the patient to perform; determining at least one step metric from the following metrics: a stress level of the patient while performing the initial step, successful completion of the initial step, the time needed to complete the initial step, and/or a quantity of errors made while carrying out the initial step; determining a subsequent step for the patient to perform immediately after the initial step based on the at least one step metric; and providing the patient with the subsequent step.

Determining the at least one step metric may comprise determining at least two of the metrics, and determining the subsequent step for the patient to perform based on the at least one step metric may comprise determining the subsequent step for the patient to perform based on the at least two step metrics.

Determining the at least one step metric may comprise determining at least three of the step metrics, and determining the subsequent step for the patient to perform based on the at least one step metric may comprise determining the subsequent step for the patient to perform based on the at least three step metrics.

Determining the subsequent step may comprise selecting the subsequent step from among a plurality of predetermined steps.

Selecting the subsequent step may comprise selecting a step of a lessor complexity based on the at least one step metric.

Selecting the subsequent step may comprise selecting a step of a greater complexity based on the at least one step metric.

The method may further comprise: after providing the subsequent step to the patient, determining at least one subsequent step metric from the following subsequent step metrics: a stress level of the patient while performing the subsequent step, successful completion of the subsequent step, the time needed to complete the subsequent step, and/or the quantity of errors made while carrying out the subsequent step; determining a further step for the patient to perform immediately after the subsequent step based on the at least one subsequent step metric; and providing the patient with the further step.

Determining the at least one step metric may comprise determining the stress level of the patient while performing the initial step. Determining the stress level of the patient while performing the initial step may comprise determining the stress level of the patient via a biosensor worn on the patient.

The method may further comprise determining a difficulty level for the patient prior to providing the patient with the initial step of the therapy set up program. Determining the difficulty level for the patient may comprise providing questions to the patient pertaining to personal details about the patient and based on responses to the questions determining the difficulty level for the patient.

As another aspect of the present invention, a system for acclimating a patient to a therapy is provided. The system comprises: a number of biosensors structured to be positioned on the patient; a controller in communication with the number of biosensors; and a user interface in communication with the controller, the user interface structured to provide information to, and receive information from, the patient, wherein the controller is programmed to: provide the patient, via the user interface, an initial step of a therapy set up program for the patient to perform; determine at least one step metric from the following metrics: a stress level of the patient while performing the initial step, successful completion of the initial step, the time needed to complete the initial step, and/or a quantity of errors made while carrying out the initial step; determine a subsequent step for the patient to perform immediately after the initial step based on the at least one step metric; and provide the patient, via the user interface, with the subsequent step.

The controller and the user interface may be components of an electronic device. The electronic device may be one of a smartphone or tablet. The user interface may be a touchscreen of the smartphone or tablet.

The controller may be at least partially cloud-based. The controller may be fully cloud-based.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
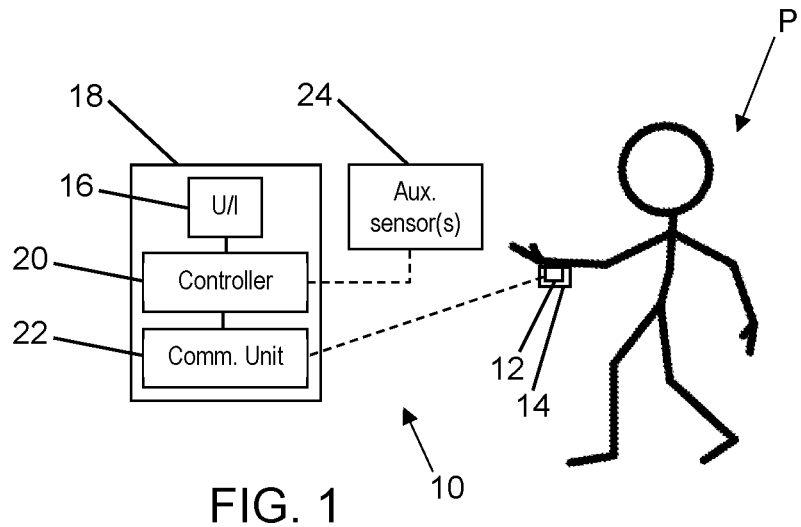
FIG. 1 is a schematic view of a system for acclimating a patient to a therapy in accordance with one example embodiment of the present invention, shown with a patient interacting therewith, with which methods in accordance with the present invention may be carried out.

As used herein, the singular form of "a", "an", and "the" include plural references unless the context clearly dictates otherwise.

As used herein, the statement that two or more parts or components are "coupled" shall mean that the parts are joined or operate together either directly or indirectly, i.e., through one or more intermediate parts or components, so long as a link occurs.

As used herein, the term "controller" shall mean a number of programmable analog and/or digital devices (including an associated memory part or portion) that can store, retrieve, execute and process data (e.g., software routines and/or information used by such routines), including, without limitation, a field programmable gate array (FPGA), a complex programmable logic device (CPLD), a programmable system on a chip (PSOC), an application specific integrated circuit (ASIC), a microprocessor, a microcontroller, a programmable logic controller, or any other suitable processing device or apparatus. The memory portion can be any one or more of a variety of types of internal and/or external storage media such as, without limitation, RAM, ROM, EPROM(s), EEPROM(s), FLASH, and the like that provide a storage register, i.e., a non-transitory machine readable medium, for data and program code storage such as in the fashion of an internal storage area of a computer, and can be volatile memory or nonvolatile memory. A controller may be in-whole or in-part in a local device or alternatively may be a cloud based arrangement in-whole or in-part.

As used herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Embodiments of the present invention provide a patient with an adaptive, interactive, guided therapy set up program. Through monitoring the patient's sympathetic activation (e.g., via a biosensor) and other factor(s) (e.g., success rate, failure rate, timing, etc.) as the patient works through the guided therapy setup program, the system automatically tailors the goals of the particular patient and provides the patient with steps of the appropriate size/difficulty to build the patient's confidence in being able to self-manage the therapy, without setting goals too small and/or too slowly for users that do not need additional help, which could otherwise cause a patient to lose interest and perhaps miss a valuable step or steps. Steps are guided through a user interface, e.g., of a smartphone, tablet, or other suitable computing arrangement where the biosensor and therapy system will be paired. At each step, the user's successful completion of the step is confirmed, the amount of time required to complete the step, the number of errors made, as well as the level of stress of the user (e.g., without limitation, average level, evolution over time, peaks, etc.) during completion is assessed. If the user completes steps quickly, successfully, and with a low stress rate, or if stress decreases during the step procedure, then certain steps can be skipped. If, instead, the user is unsuccessful, takes a long time to complete, or has a high measured stress level, then either a step back in the acclimation process is taken or the next step to be completed is smaller.

Referring now to FIG. 1, a system 10 for acclimating a patient P to a therapy in accordance with one example embodiment of the present invention, shown with patient P interacting therewith, with which methods in accordance of the present invention may be carried out, is shown. System 10 includes a number of biosensors 12 positioned on patient P that are capable of measuring anxiety, stress, or a derivative of either of those, such as heart rate variability (HR(V)) or galvanic skin response. In the example shown in FIG. 1, the number of wearable biosensors 12 are provided as a portion of a wearable device 14, which in such example is a smartwatch such as manufactured and sold by, for example, without limitation, Apple, FitBit, Garmin, etc., and that is worn on the wrist of patient P. It is to be appreciated, however, that the particular arrangement illustrated in the example embodiment of FIG. 1 is provided for exemplary purposes only and that one or more of the quantity of biosensors 12, arrangement(s) in which they are provided, and/or the location(s) of biosensor(s) 12, or relative to, patient P may be varied without varying from the scope of the present invention.

Continuing to refer to FIG. 1, system 10 further includes a user interface 16 (U/I) of an electronic device 18, e.g., without limitation, a touchscreen of a smartphone or tablet computer, a keyboard and display of a laptop, or any other suitable user interface associated with a computing arrangement. User interface 16 is structured to provide information to, and receive information from patient P. Electronic device 18 also includes a controller 20 in communication with user interface 16 for processing information received from, and providing information to, user interface 16, as well as a communication unit 22 which may be provided as a portion of, or as a separate element in communication with, controller 20. Communication unit 22 provides for communication between controller 20 and other elements of system 10, such as the number of biosensors 12, and other external devices or cloud computing/storage services via the internet, cellular, WiFi, Bluetooth®, or any other wireless or wired arrangement(s). For example, without limitation, communication unit 22 may facilitate communication with the number of biosensors 12. Communication unit 22 may also facilitate communication with external devices whether local or distant, directly or via a network. Although shown only as a portion of electronic device 18, it is to be appreciated that controller 20 may instead be provided remotely in-part or generally completely remotely as a cloud-based computing arrangement.

In addition to the elements previously described, system 10 may include a number of auxiliary sensors 24 in communication (directly or indirectly, wired or wirelessly) with controller 20 for monitoring patient P. Such sensor(s) 24 may be provided as a portion of electronic device 18 (e.g., image sensor(s), IR sensor, microphone, etc.) or separate from electronic device 18 (e.g., image sensor(s), IR sensor, microphone, accelerometer, temperature sensor, etc.).

Figure 2:
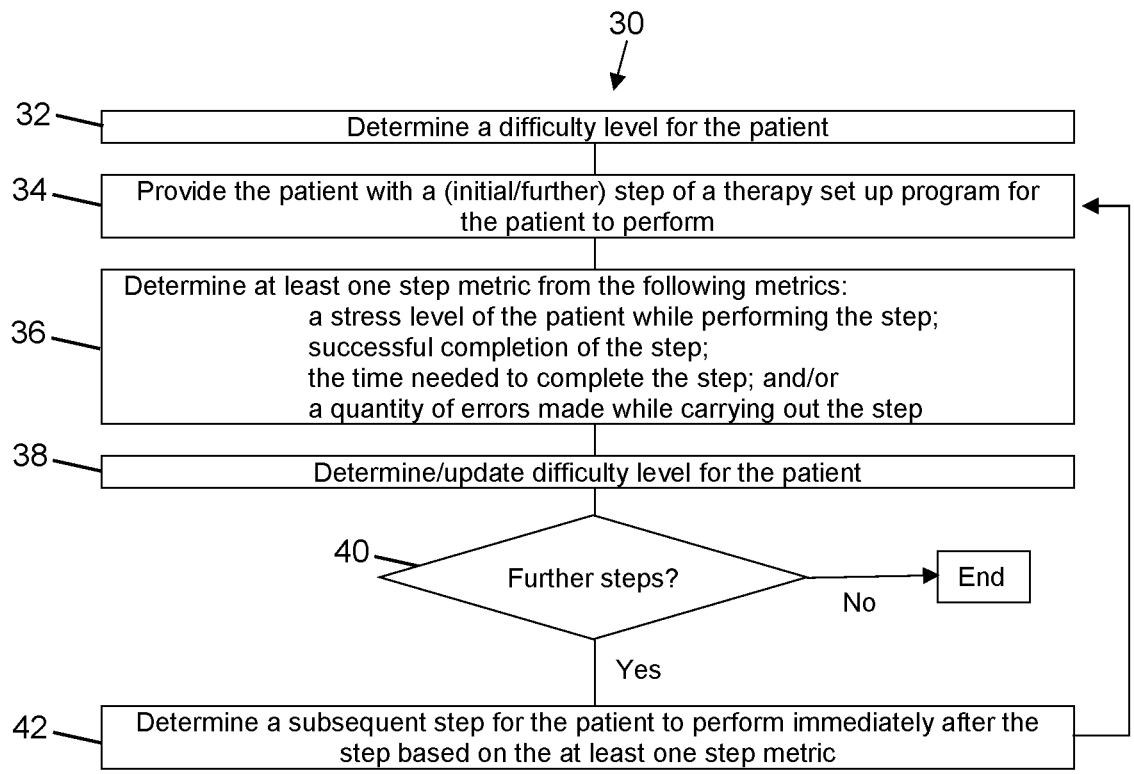
FIG. 2 is a flow chart showing the general steps of a method of acclimating a patient to a therapy in accordance with one example embodiment of the present invention that may be carried out using the system of FIG. 1.

Having thus described a general overview of a system in accordance with an example embodiment of the present invention, an example method 30 of acclimating a patient to a therapy in accordance with one example embodiment of the present invention that may be carried out using system 10 of FIG. 1 will now be described in conjunction with the flow chart of FIG. 2 in addition to FIG. 1. Depending on the particular application/embodiment, method 30 may generally begin at step 34 wherein patient P is provided with an (initial) step of a therapy set up program for patient P to perform. The (initial) step may be provided via user interface 16 as one or both of video and/or sound instruction and/or demonstration of the action to be carried out by patient P. The (initial) step may be a predetermined (initial) step of a fixed difficulty level that is presented to all patients. Alternatively, as shown in step 32, step 34 may be preceded by a prior step in which a starting difficulty level likely suitable for patient P is determined. In such case the (initial) step provided to patient P would be of a corresponding difficulty level to the level determined in step 32. Such determination made in step 32 can occur in several ways without varying from the scope of the present invention. For example, without limitation, such determination may be made based in-whole or in-part on response to questions presented to patient P (e.g., via user interface 16) regarding details about themselves, e.g., their education level, comfort level with medical devices/treatments, demographics details, etc. Alternatively and/or additionally, details of the user contained in a local or cloud based database regarding the patient themself and/or previous acclimation trainings may be used.

Once patient P has been provided with the (initial) step at 34, one or more step metrics of patient P related to patient P carrying out the (initial) step are monitored/determined by controller 20. Such metrics may include one or more of: a stress level of the patient while performing the initial step, as can be determined from one or more of the number of biosensors 12; successful completion of the initial step, as determined from an indication provided directly or indirectly by patient P (e.g., by selecting a done/next box, by controller 20 receiving an indication from a sensor or related device that an action as occurred, etc.); the time needed to complete the step (e.g., from a timer in controller 20 that starts when the step is provided and stops upon the indication of completion of the step or from a manual input from the user); and/or a quantity of errors made while carrying out the initial step (e.g., as self-reported by patient P, as detected by sensors, etc.).

Next, as shown at step 38, the difficulty level for patient P is determined/updated based on one or a combination of the step metric(s) determined at 36. As an example, if patient P exhibited an elevated stress level, took longer than a predetermined time, failed to complete the step, and/or made several errors, the difficulty level and or length (e.g., amount of content) of the subsequent step would be reduced, so as to not potentially overwhelm patient P. Alternatively, if patient P exhibited a reduced stress level, took less than a predetermined time, successfully completed the step, and/or made no errors, the difficulty level and or length (e.g., amount of content) of the subsequent step may be increased, so as to not potentially not lose the interest of patient P. As a further alternative, if one or more of the step metrics of patient P fell generally along predetermined values, thus indicating the difficulty level is perhaps appropriate for patient P, the difficulty level of the (initial) step may be carried on to the subsequent step.

After the difficulty level for patient P has been determined/updated at 38, a check is made if the last step performed/carried out by patient P was the last step of the therapy set up program, or alternatively if there are steps yet to be performed, such as shown at 40. If the last step performed/carried out by patient P is the final step of the therapy set up program or it is determined that there are no further steps, method 30 ends. If it is determined that there are further steps to be performed/carried out by patient P, method 30 continues on to step 42 wherein the next/subsequent step is determined based on the difficulty level of the patient determined/updated at step 38 (i.e., based on the one or more step metrics determined in step 36). The method then generally loops back to step 34 where the therapy set up program step determined in step 42 is provided (e.g., via user interface 16) to patient P to perform/carry out. Method 30 then continues on in a loop with each subsequent step of the therapy set up program being adjusted for patient P as needed until it is determined that there are no further steps left in the therapy set up program for patient P to perform, and thus method 30 ends. Although such determination to continue or end method 30 is shown occurring between steps 38 and 42, it is to be appreciated that such determination step could generally occur at any point in method 30 as long as all of the steps of the therapy set up program are at least provided to patient P without varying from the scope of the present invention (i.e., step metrics from the last step of the therapy set up program do not have to be obtained/determined, although such information may be of value for other patients and/or future therapy set up programs for patient P and thus determined).

Figure 3:
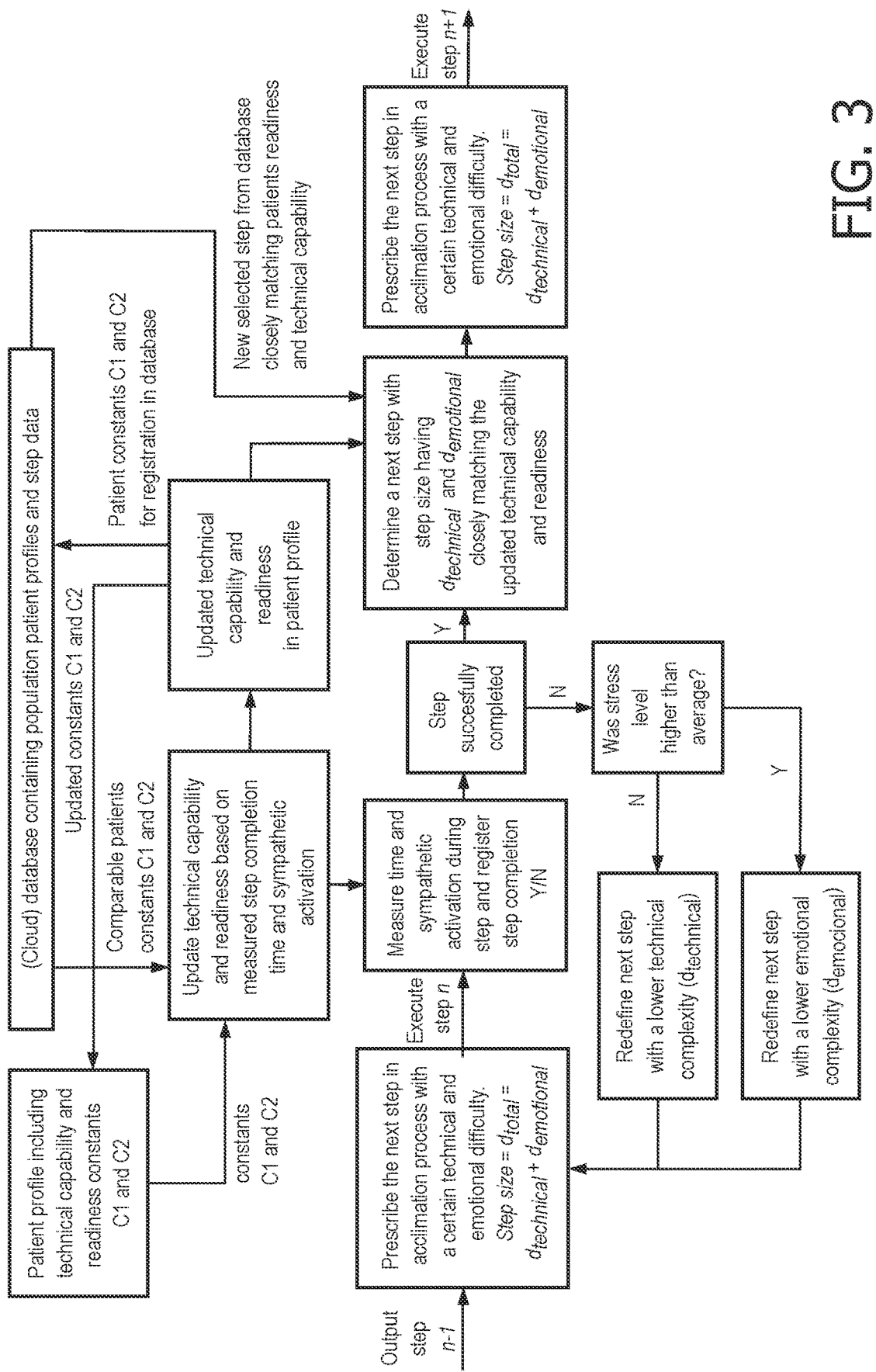
FIG. 3 is a flow chart showing detailed steps of another method in accordance with another example embodiment of the present invention which may be carried out using a system such as shown in FIG. 1.
Figure 4:
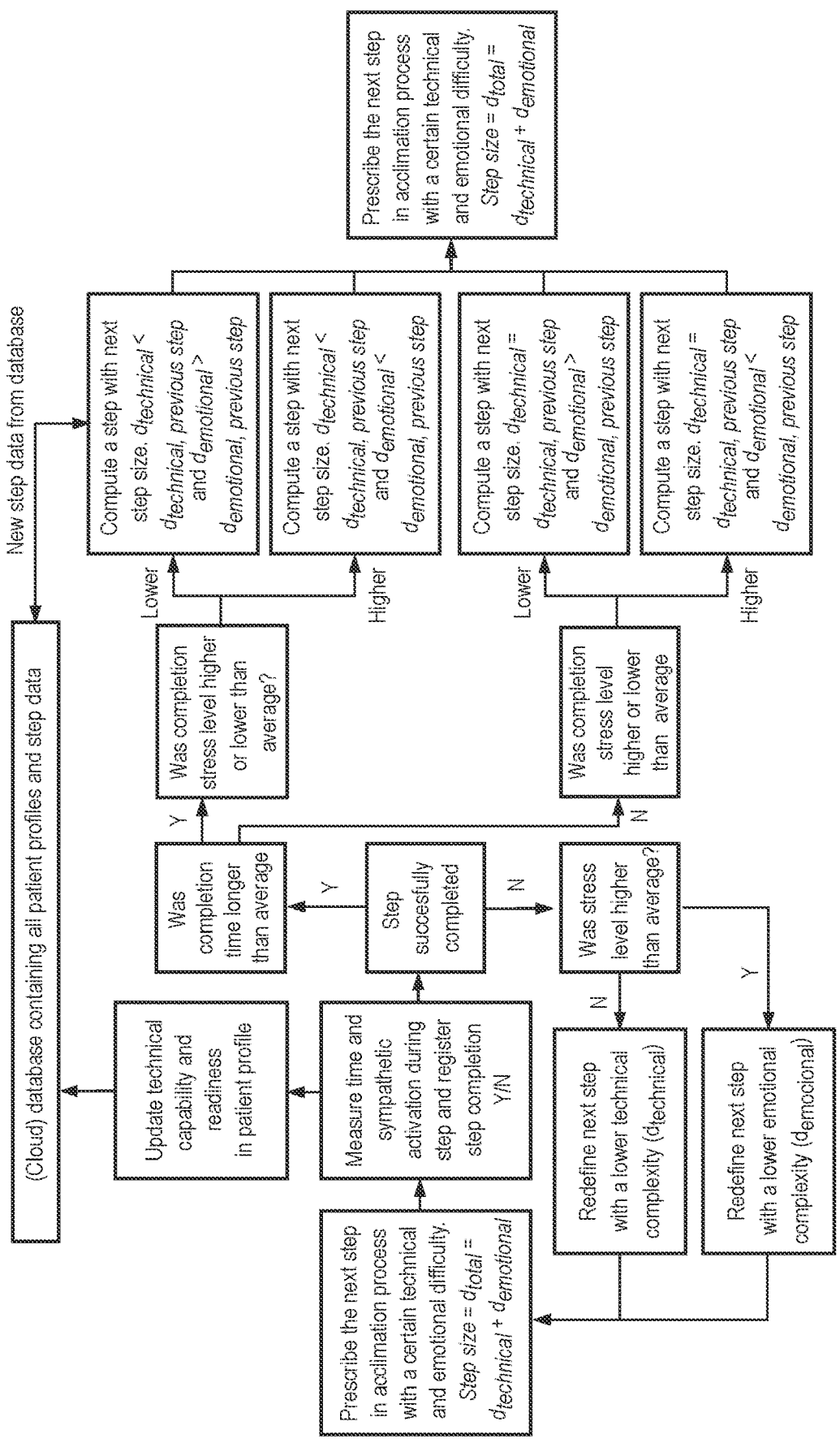
FIG. 4 is a flow chart showing detailed steps of yet another method in accordance with yet another example embodiment of the present invention which may be carried out using a system such as shown in FIG. 1.

FIGS. 3 and 4 show some further more detailed examples of flow charts for methods similar to method 30 in accordance with further embodiments of the present invention that may be carried out using system 10 such as shown in FIG. 1. Once again, through monitoring sympathetic activation and/or success rate of patient P as they walk through the guided therapy setup program, system 10 (i.e., controller 20) automatically tailors patients' goals and gives everyone the right size steps to build their confidence in being able to self-manage the therapy, without setting goals too small and too slowly for users that do not need additional help. Steps are guided through user interface 16. At each step, one or more of the user's successful completion of the step is confirmed, amount of time required to complete, number of errors made, as well as their level of stress (average level, evolution over time, peaks, etc.) during completion is assessed. If the user completes steps quickly, successfully, and with a low stress rate, or if stress decreases during the step procedure, then certain steps can be skipped. If, instead, the user is unsuccessful, takes a long time to complete, or has a high measured stress level, then either a step back in the acclimation process is taken or the next step to be completed is smaller.

In an example embodiment, the steps are automatically determined based on a predicted success rate based on an ongoing profile built for the patient. Profile dimensions include technical ability and readiness. Technical ability is a function of task completion success rate, task technical difficulty, and/or task completion time. Readiness is a function of task completion success, task emotional/anxiety difficulty, and monitored sympathetic activation during task description, task attempt, and task follow-up. Next step is determined by current patient profile and profile of the next set of tasks (technical and emotional difficulty).

As an example: for a certain step in the set-up the "step size' is for instance the total step difficulty, which is the sum of the technical and emotional difficulty:

$$\text{Step size} = d_{total} = d_{technical} + d_{emotional} \quad (1)$$

The technical difficulty is for instance specified by both the average time taken until completion and the amount of errors/retries before success across the patient population. The emotional difficulty is for instance specified by the average measured sympathetic activation during this step across the patient population. The current patient's technical capability and readiness are for instance specified as:

$$\text{Technical capability} = C1 \times \left( \frac{1}{\text{average task completion time}} + \text{success rate} \right) \quad (2)$$

$$\text{Readiness} = C2 \times \frac{1}{\text{sympathetic activation}} \quad (3)$$

For the upcoming step, the technical difficulty must be smaller than the technical capability ($d_{technical}$<technical capability) and the emotional difficulty is smaller than the emotional capability ($d_{emotional}$<readiness). Both conditions together define the upper limit of the upcoming step size. If the upcoming step in the procedure has an emotional or technical difficulty that is greater than the readiness or technical capability the step needs to be split into multiple smaller steps to improve chance of success (i.e. both technical and emotional limits are satisfied). Constants C1 and C2 are related to the personal profile of the patient. These constants are updated after each step based on the population average equivalent step size.

For example a patient is attempting a step with an estimated equivalent size of '2', which is known to be equally technically and emotionally difficult (i.e. $d_{technical}$=1 and $d_{emotional}$=1, data from previous attempts by other patients). If the patient takes a long time to complete the task but does not show elevated stress levels this patients profile may now be updated by reducing C1, because the patient seems to take longer than average to complete steps. The next step that is offered may be smaller than average to avoid that the patient becomes demotivated because the ask is too difficult. For instance if the next step in the procedure is a technically difficult but non-stressful step, this step may be split into multiple small steps. If however, the patient completes the step in quickly but with a high stress level the patients profile will be updated by decreasing C2 but increasing C1. The same next step may be completed in full by this patient or the step size may even be increased, effectively incorporating more technical tasks into the next step, and there is no need to split the step into smaller parts. However, if the next step is more emotionally difficult than technically difficult, the step may need to be cut into smaller pieces, thus reducing the step size to lower than the readiness of the patient. The high stress level of the patient makes this step more challenging.

For instance, the patients technical capability and readiness may be adjusted based on the following rules:

1) If the task completion time is shorter than the average task completion time for this step for patients with comparable profiles, then the constant C1 is raised by a fixed amount, for instance 25% or alternatively by an amount proportional to the difference in the patient's completion time vs the time for the comparable users.
2) If the task completion time is longer than the average task completion time for this step for patients with comparable profiles, then the constant C1 is lowered by a fixed amount, for instance 25% or alternatively by an amount proportional to the difference in the patient's completion time vs the time for the comparable users.
3) If the task completion time is comparable to the average task completion time for this step for patients with comparable profiles, then the constant C1 is not changed.
4) If the sympathetic activation is lower than the average sympathetic activation for this step for patients with comparable profiles, then the constant C2 is raised by a fixed amount, for instance 25% or alternatively by an amount proportional to the difference in the patient's sympathetic activation vs the sympathetic activation for the comparable users.
5) If the sympathetic activation is higher than the average sympathetic activation for this step for patients with comparable profiles, then the constant C2 is lowered by a fixed amount, for instance 25% or alternatively by an amount proportional to the difference in the patient's sympathetic activation vs the sympathetic activation for the comparable users.
6) If the sympathetic activation is comparable to the average sympathetic activation for this step for patients with comparable profiles, then the constant C2 is not changed.

The next step in the sequence can be selected from an existing database containing all possible steps and associated emotional and technical difficulties. From this database a next step is selected with a technical difficulty that is close to, but not higher than, the patients technical capability.

As an example in connection with a patient/user starting a positive airway pressure (PAP) therapy. Starting PAP can be very scary for certain patients, especially setting up the PAP equipment and the first session of therapy. The setup process is segmented into steps. Steps are guided through a "Welcome to PAP app". Steps for success could include, for example, without limitation—pairing the biosensor, unboxing the mask, placing the mask on the face and fitting (video confirmation) [detailed fitting steps available per mask], getting connected to the device, turning the machine on, watch a tv show with the PAP on and attached, wear the mask for 30 minutes in bed, etc. Each step has a rated Technical complexity and an anticipated emotional difficulty. Note the numbers in below example are in normalized units, although other units and scales can be used in the invention as well.

One step in this process is the fitting of the mask. One such step in the fitting process could be to briefly place the mask on the face, which is followed by a full fitting procedure. As an example of the present invention a patient has completed the step of placing the mask on the face. In this step the biosensor measures the sympathetic activation during the mask placement and the user is asked to manually time the procedure. The step is ranked as having average technical difficulty (i.e. 5, arbitrary scale). The emotional difficulty is rated higher than average (i.e. 7, as it is known that many users struggle with the feeling of the mask on the face, knowing that they will be wearing the mask during night. The patient profile includes constants C1=2.3 and C2=5, as a result of the patient characteristics such as age and gender and any other information that is stored in the patient profile and as a result of previous steps taken in the process. These constants would be typical for a person with a moderate technical capability but a relatively low readiness, i.e., someone who is potentially stressed or unconfident. Population average completion times (for comparable patient profiles) are 0.55 (on a normalized 0-1 scale) and the success rate of the patient up to this step has been 0.55 (i.e. 55% of previous attempts at completing a step were successful. Population average sympathetic activation for this step is 0.7. The database of steps after the current steps includes:

TABLE 1

Step Database

| Option | Step description | $d_{technical}$ | $d_{emotional}$ |
|---|---|---|---|
| 1 | Putting on the headgear and leaving on to get familiar for 2 minutes before removing headgear and proceeding to next step | 5 | 4 |
| 2 | Putting on the headgear, briefly fitting and continuing to next step without waiting | 5 | 6 |
| 3 | Putting headgear on and waiting for 2 minutes to attach mask | 8 | 7 |
| 4 | Putting headgear on and attaching mask immediately | 8 | 10 |
| 5 | Putting on headgear and mask and tightening straps to therapy level tightness | 10 | 12 |
| 6 | Assembling headgear, mask and hose and attaching to machine (off head) | 10 | 3 |

In the numbered examples below, several different scenarios are presented, each following the logic of embodiments of the present invention.
1) The patient has completed the mask placement in an average time (0.5) and without notably higher than normal sympathetic activation (0.72). In this case both C1 and C2 are not updated, resulting in a technical capability of 5.4 and an emotional capability of 6.9. A fitting next step is defined with technical and emotional difficulty similar to the previous step, i.e., option 2: placing the headgear on the head and continuing to the next step without waiting.
2) The patient has completed the mask placement in a faster than average time (0.35) and without notably higher than normal sympathetic activation (0.7). In this case C1 is updated for instance by increasing with 25% and C2 is not updated, resulting in a technical capability of 9.8 and an emotional capability of 7.1. A fitting next step is with higher technical difficulty and comparable emotional difficulty, i.e. option 3: placing the headgear on the head and waiting for 2 minutes to attach the mask before continuing on to the next step, so that the patient has time to get comfortable with the headgear before attaching the mask (but without needing an extra step with extra instructions to attach the mask because the patient has a high technical capability).
3) The patient has completed the mask placement in a faster than average time (0.35) and with lower than normal sympathetic activation (0.5). In this case C1 and C2 are updated for instance by increasing with 25%, resulting in a technical capability of 9.8 and an emotional capability of 12.5. A fitting next step is with higher technical and emotional difficulty, i.e., option 4: placing the headgear on the head attaching the mask immediately before continuing on to the next step, so the patient can move swiftly through the setup process.
4) The patient has completed the mask placement in a faster than average time (0.3) and with higher than normal sympathetic activation (0.95). In this case C1 is updated for instance by increasing with 25% and C2 is updated for instance by decreasing with 25%, resulting in a technical capability of 11.2 and an emotional capability of 3.8. A fitting next step is with higher technical and lower emotional difficulty, i.e., option 4: Assembling headgear, mask and hose and attaching to machine (off head), so the patient can get more familiar with the machine and accessories before attempting to put on the headgear.
5) The patient fails the task. The current step is reduced in step size and the patient is offered a new step based on the options in the database (i.e. a different list of options than in the above table). For instance if the patient showed low stress but was unable to complete the task, the patient is given a technically easier step, for instance by following a more detailed, step by step instruction of how to place the mask on the face. If the patient showed high stress during the failed task, more thorough emotional guidance is given (for instance by using paced breathing during the placement or by showing videos of peers who address concerns they once had about comfort before use.

The full database of optional steps includes all possible steps from initiation for instance starting with collecting all the hardware to completion, i.e. when the patient is ready to use PAP therapy. Each time the performance of the patient during the previous step dictates which step they are offered next and how they will advance through the therapy.

In contrast to the embodiment described above where the stress level of the patient/user is used as input to the next step and the next step size is reduced if the patient is not ready enough to perform the next full task, in another example embodiment of the present invention the stress level of the patient/user is monitored during task execution and the patient is guided to a lower stress state while completing the task. For instance if the patient readiness (equation 3 above) is lowered (due to increased sympathetic activation), the patient is prompted to reduce their stress using biofeedback, for instance controlled breathing techniques. For example, without limitation, in a PAP application, before wearing the mask for the first time, the patient is guided towards a lower stress state by using biofeedback based relaxation techniques until they are in a low stress state and are ready to wear the mask. If the stress state increases after donning the mask the patient is encouraged to restart the relaxation techniques to return to a lower stress state and complete the task as planned.

From the foregoing description and examples it is thus to be appreciated that embodiments of the present invention provide interactive/reactive systems and methods for remotely guiding a patient through an unsupervised therapy program that improve upon conventional solutions.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of acclimating a patient to a positive pressure therapy, the method comprising:
    providing the patient with a positive pressure therapy system, including a positive pressure generating device a mask, a headgear, and a hose;
    providing the patient with a wrist-worn, body-worn, or head-worn sensor;
    providing the patient with a user interface capable of communicating with the patient orally, visually, or both orally and visually;
    instructing the patient to unbox or assemble the positive pressure therapy system;
    monitoring a biological metric of the patient while the patient is unboxing or assembling the positive pressure therapy system using the sensor;
    determining a stress level of the patient while unboxing or assembling the positive pressure therapy system based on the monitored biological metric,
    selecting one of at least two possible subsequent steps to give to the patient based on the stress level, wherein the two subsequent steps include (a) instructing the patient to don the mask and the headgear and wait to turn on the positive pressure therapy device, or (b) instructing the patient to don the mask and the headgear and immediately turn on the positive pressure therapy device; and
    providing the patient the subsequent step instruction via an oral prompt, a written prompt, or both an oral and written prompt via the user interface.

2. The method of claim 1, further comprising monitoring a performance metric from the group consisting of: successful completion of the unboxing or assembling the positive pressure therapy system using the sensor; the time needed to complete the unboxing or assembling the positive pressure therapy system using the sensor, and a quantity of errors made while unboxing or assembling the positive pressure therapy system using the sensor, wherein selecting one of at least two possible subsequent steps is based on both the biological metric and the performance metric.

3. A system for acclimating a patient to a therapy, the system comprising:
    a wrist-worn, body-worn, or head-worn sensor structured to be positioned on the patient;
    a controller in communication with the wrist-worn, body-worn, or head-worn sensor; and
    a user interface in communication with the controller, the user interface structured to provide information to, and receive information from, the patient,
    wherein the controller is programmed to:
        instruct the patient the patient, via the user interface, to unbox or assemble the positive pressure therapy system;
        monitor a biological metric of the patient via the wrist-worn, body-worn, or head-worn sensor while the patient is unboxing or assembling the positive pressure therapy system;
        determine a stress level of the patient while unboxing or assembling the positive pressure therapy system based on the monitored biological metric;
        selecting one of at least two possible subsequent steps to give to the patient based on the stress level, wherein the two subsequent steps include (a) instructing the patient to don the mask and the headgear and wait to turn on the positive pressure therapy device, or (b) instructing the patient to don the mask and the headgear and immediately turn on the positive pressure therapy device; and
        provide the patient, via the user interface, the selected subsequent step.

4. The system of claim 3, wherein the controller and the user interface are components of an electronic device.

5. The system of claim 4, wherein the electronic device is one of a smartphone or tablet.

6. The system of claim 3, wherein the controller is at least partially cloud-based.

* * * * *